United States Patent [19]

Kallenbach

[11] Patent Number: 5,574,201
[45] Date of Patent: Nov. 12, 1996

[54] ALKYLATION PROCESS

[75] Inventor: Lyle R. Kallenbach, Bartlesville, Okla.

[73] Assignee: Phillips Petroleum Company, Bartlesville, Okla.

[21] Appl. No.: 440,262

[22] Filed: May 12, 1995

[51] Int. Cl.$^6$ .................................................. C07C 2/62
[52] U.S. Cl. ......................... 585/730; 585/721; 585/731
[58] Field of Search ....................... 585/730, 731, 585/721

[56] References Cited

U.S. PATENT DOCUMENTS

| | | | |
|---|---|---|---|
| 3,457,317 | 7/1969 | Hoffmann et al. | 260/666 |
| 4,270,014 | 5/1981 | Norton et al. | 585/22 |
| 4,357,481 | 11/1982 | Kramer | 585/724 |
| 5,220,095 | 6/1993 | Hommeltoft et al. | 585/720 |
| 5,233,119 | 8/1993 | Kallenbach et al. | 585/721 |
| 5,349,116 | 9/1994 | Kallenbach et al. | 585/730 |

*Primary Examiner*—Asok Pal
*Assistant Examiner*—In Suk Bullock
*Attorney, Agent, or Firm*—K. K. Brandes

[57] ABSTRACT

The alkylation of $C_2$–$C_{12}$ alkanes (preferably isobutane) with $C_2$–$C_{12}$ alkenes (preferably butene-2), in the presence of trifluoromethanesulfonic acid on a solid inorganic material as catalyst, is carried out with dicyclopentadiene and/or tetrahydrodicyclopentadiene as additional alkylating agent(s).

19 Claims, No Drawings

ALKYLATION PROCESS

BACKGROUND OF THE INVENTION

This invention relates to an improved process for alkylating alkanes with alkenes in the presence of a supported sulfonic acid catalyst.

The alkylation of alkanes (paraffins) with alkenes (monoolefins) in the presence of supported trifluoromethanesulfonic acid catalysts is known and is disclosed in U.S. Pat. Nos. 5,220,095, 5,233,119 and 5,349,116. The alkylates produced by these known alkylation processes are useful as motor fuels. However, there is an ever present need for improving these processes so as to produce alkylates having lower vapor pressure (thus complying with increasingly stringent environmental regulations). The present invention is a process improvement directed toward this goal.

SUMMARY OF THE INVENTION

It is an object of this invention to provide an improved process for alkane/alkene alkylation in the presence of a supported trifluoromethanesulfonic acid catalyst, wherein at least one cyclic hydrocarbon is present during the alkylation reaction. It is another object of this invention to produce alkylates having a lower content of volatile hydrocarbons (in particular isopentane) than alkylates produced in corresponding reactions without said cyclic hydrocarbon(s). Other objects and advantages will be apparent from the detailed description and the appended claims.

According to this invention, in a process for alkylating at least one feed alkane containing 2–12 carbon atoms per molecule with at least one feed alkene containing 2–12 carbon atoms per molecule in the presence of a catalyst comprising trifluoromethanesulfonic acid and at least one solid inorganic material so as to produce at least one product alkane containing more carbon atoms that said at least one feed alkane, the improvement comprises the presence of at least one tricyclic hydrocarbon selected from the group consisting of dicyclopentadiene (also known as tricyclo [5.2.1$^{2,6}$]deca-3,8-diene) and tetrahydrodicyclopentadiene (also known as tricyclo[5.2.1$^{2,6}$]decane) in the feed comprising said at least one alkane and said at least one alkene. Preferably, the content of said at least one tricyclic hydrocarbon in the feed is about 0.05 to about 3.0 weight-%.

DETAILS OF THE INVENTION

The catalyst composition employed in the process of this invention comprises (preferably consists essentially of ) $CF_3SO_3H$ on a solid inorganic carrier material. The solid inorganic material can be alumina, silica (presently preferred), silica-alumina, titania, zirconia, aluminum phosphate, aluminum oxide/phosphate, aluminum borate, aluminum borate/oxide, boron oxide, boron phosphate, aluminum boron phosphate, boron sulfate, zirconium sulfate and mixtures thereof. Most of these solid inorganic materials are either commercially available or can easily be prepared by one skilled in the art. The preparation of aluminum oxide/phosphate (also known as aluminum phosphate/oxide) is described in U.S. Pat. No. 5,254,794. The preparations of boron phosphate on silica and of boron sulfate on silica are described in U.S. Pat. No. 5,233,119. The preparation of aluminum borate/oxide on alumina described in U.S. Pat. No. 5,349,116. Generally, the surface area of these solid inorganic materials is in the range of about 200 to about 400 m$^2$/g (determined by the BET method of Brunauer Emmett and Teller employing $N_2$). Preferably, the particles of these solid material have a size in the range of about 0.4 mm to about 0.8 mm (i.e., smaller than about 20 mesh and larger than about 40 mesh).

The catalyst compositions employed in the process of this invention can be prepared in any suitable manner. Generally, the solid inorganic material is first dried (preferably for about 0.1–20 hours at a temperature of about 100°–150° C.) and calcined (preferably for about 2–6 hours at a temperature of about 450°–600° C., more preferably about 480°–570° C., either in air or in a $N_2$ atmosphere). Thereafter, the solid inorganic material is combined with $CF_3SO_3H$ in any suitable manner. Generally, $CF_3SO_3H$ is added in liquid form to the top layer of the solid inorganic material (preferably being present in a catalyst bed) just prior to the alkylation reaction, generally at a weight ratio of $CF_3SO_3H$ to said solid inorganic material in the range of about 0.01:1 to about 0.4:1 (preferably about 0.02:1 to about 0.1:1).

Any of the above-described compositions can be employed as catalyst in the alkylation process of this invention. The process for alkylating $C_2$–$C_{12}$ alkanes (preferably isoalkanes, i.e., branched alkanes) with $C_2$–$C_{12}$ alkenes (preferably those containing an internal double bond), in the presence of dicyclopentadiene or tetrahydrodicyclopentadiene or any mixtures of these two tricyclic hydrocarbons, can be carried out in any suitable manner. The fluid feed comprising at least one $C_2$–$C_{12}$ alkane, at least one $C_2$–$C_{12}$ alkene and at least one of the above-described tricyclic hydrocarbons is contacted with any of the above-described catalyst compositions at effective alkylation conditions, generally at a relatively low temperature of up to about 100° C., preferably about −20° C. to about 100° C. (more preferably about 0°–30° C.), generally at an absolute pressure of about 2–8 atm (equivalent to about 15–103 psig). Generally, the molar ratio of feed alkane(s) to feed alkene(s) is in the range of about 6:1 to about (12:1), preferably about 8:1 to about 10:1. Generally, the content of the tricyclic hydrocarbon(s) in the feed is in the range of about 0.05 to about 3.0 weight-% (preferably about 0.1–1.0 weight-%), of dicyclopentadiene or tetrahydrodicyclopentadiene or mixtures thereof.

The feed components, i.e., alkane(s), alkene(s) and tricyclic hydrocarbon(s), can be combined in any suitable manner so as to provide the fluid alkylation feed. The fluid (preferably liquid) feed, which comprises alkane(s), alkene(s) and tricyclic hydrocarbon(s), can be contacted with the catalyst composition in any suitable mode, preferably in a fixed catalyst bed operation in which the feed mixture flows downward through a solid catalyst layer, generally at a liquid hourly space velocity of about 0.5–5 (preferably about 1–3) cm$^3$ feed per cm$^3$ catalyst composition per hour. The alkylation process can be carried out in a continuous manner or as a batch process. Generally, the $CF_3SO_3H$ component moves as a zone along the solid catalyst bed in the direction of the alkylation feed. When the $CF_3SO_3H$ zone approaches the exit region of the catalyst bed, the reactant flow can be reversed (so that the $CF_3SO_3H$ zone can travel back through the catalyst bed).

Suitable feed alkanes are normal (straight-chain) alkanes and isoalkanes (i.e., branched) alkanes, each containing 2–12 carbon atoms per molecule. Non-limiting examples of suitable alkanes are propane, n-butane (i.e., normal-butane), isobutane, n-pentane, isopentanes (2-methylbutane and 2,2-dimethylpropane), n-hexane, isohexanes (such as 2-methylpentane, 3-methylpentane, 2,2-dimethylbutane), n-heptane and isoheptanes (such as methyl-substituted hexanes and dimethyl-substituted pentanes), n-octane, isooctanes, n-nonane, isononanes, n-decane, isodecanes, n-undecane, isoundecanes, n-dodecane, isododecanes and mixtures thereof. Presently preferred are branched $C_4$–$C_8$ alkanes. Particularly preferred is isobutane.

Suitable feed alkenes are normal (straight chain) and branched alkenes containing one C=C double bond and 2–12 carbon atoms per molecule. Non-limiting examples of suitable alkenes are propylene, butene-1, butene-2, isobutylene (isobutene), pentene-1, pentene-2, isopentenes, hexene-1, hexene-2, hexene-3, isohexenes, n-heptenes, isoheptenes, n-octenes, isooctenes, n-nonenes, isononenes, n-decenes, isodecenes, undecenes, dodecenes and mixtures thereof. Preferred alkenes are those containing 4–6 carbon atoms per molecule. Particularly preferred are butenes (more preferably butene-2).

Dicyclopentadiene (in the endo form and/or exo form) sometimes is present in relatively small amounts in refinery process streams and can be isolated therefrom (if desired). Tetrahydrodicyclopentadiene (in the endo and/or exo form) can be prepared by catalytically hydrogenating dicyclopentadiene (preferably by employing a dispersed nickel-on-kieselguhr catalyst, which is marketed by United Catalysts Inc., Louisville, Ky. under the product designation "G-49B"; essentially in accordance with the procedure described in U.S. Pat. No. 4,270,014, Column 3). It is within the scope of this invention to have dicyclopentadiene and/or tetrahydrodicyclopentadiene present as impurities in a refinery stream which is used to prepare the alkane/alkene feed. If only cyclopentadiene is present as an impurity in this stream, it is within the scope of this invention to separate at least a portion of dicyclopentadiene from the stream, hydrogenating the separated dicyclopentadiene to tetrahydrodicyclopentadiene (as described above), and combining the formed tetrahydrodicyclopentadiene (together with unconverted dicyclopentadiene) with the other feed components and introducing the entire feed mixture into an alkylation reactor.

The alkylation process of this invention generally generates a multitude of hydrocarbon products containing a greater number of carbon atoms per molecule than the feed alkane(s), as is demonstrated in the examples. Thus it is generally desirable to separate various hydrocarbon product fractions from one another and from unconverted feed hydrocarbons. This separation can be carried out in any suitable manner generally by fractional distillation, as can easily be determined by persons skilled in the various liquid-liquid separation technologies. In a preferred embodiment, the more desirable alkane products which contain 6–9 carbon atoms per molecule, which are useful as gasoline blending components, are separated from less desirable higher and lower alkanes and from unconverted feed hydrocarbons.

The following examples are provided to further illustrate the process of this invention, and are not to be construed as unduly limiting the scope of this invention.

EXAMPLE I

This example illustrates the effects of the presence of dicyclopentadiene (DCP) in the alkylation process of this invention. A U-shaped stainless steel reactor tube (inner diameter: 0.3 inch; length: 60 inches) was filled with about 26 grams of silica (20/40 mesh silica gel, Grade 57, provided by Davison Chemical Company, a division of W. R. Grace and Co.) which had been calcined in air for 4 hours at 500° C. About 2.0 $cm^3$ of trifluoromethanesulfonic acid was then added to the top (entrance) zone of the packed column while $N_2$ gas passed through the column. The entire column was maintained at a temperature of about 34° F. A liquid alkylation feed containing about 900 g isobutane, about 100 g butene-2 and 0–10 g dicyclopentadiene was pumped through the packed column at a rate of 1 $cm^3$ per minute. The exiting alkylation product (obtained at a reaction temperature of about 34° F. and a reaction pressure of about 100 psig) was cooled to about −108° F. (by means of a coolant containing solid $CO_2$ and acetone) and was then analyzed by means of a gas chromatograph and by simulated distillation (at atmospheric pressure). Each test run lasted about 16 hours. Pertinent test results are summarized in Table 1.

TABLE I

| Wt-% DCP in Feed | Alkylation Product Composition (Wt-%)[1] | | | | Olefin Conversion (%) | Reid Vapor Pressure[3] | Octane Number[4] |
| --- | --- | --- | --- | --- | --- | --- | --- |
| | $C_2$–$C_4$ Alkanes | Isopentanes | $C_6$–$C_9$ Alkanes[2] | $C_{10}^+$ Hydrocarbons | | | |
| 0 | 4.3 | 6.6 | 84.8 | 4.3 | 100 | 3.8 | 89.7 |
| 0 | 5.1 | 8.1 | 82.6 | 4.2 | 100 | 4.4 | 92.6 |
| 0 | 5.3 | 8.1 | 76.1 | 10.5 | 100 | 4.3 | 92.4 |
| 0 | 3.3 | 6.9 | 83.5 | 6.3 | 100 | 3.9 | 93.1 |
| Average: | 4.5 | 7.4 | 81.8 | 6.3 | 100 | 4.1 | 92.0 |
| 0.1 | 7.2 | 5.5 | 83.1 | 4.2 | 100 | 4.1 | 87.7 |
| 0.1 | 2.9 | 3.4 | 81.6 | 12.1 | 100 | 2.8 | 86.1 |
| 0.1 | 2.1 | 3.7 | 80.3 | 13.9 | 100 | 3.0 | 86.0 |
| 0.1 | 3.7 | 4.5 | 70.4 | 21.4 | 100 | 3.2 | 86.0 |
| Average: | 4.0 | 4.3 | 78.9 | 12.9 | 100 | 3.3 | 86.5 |
| 0.5 | 2.2 | 1.6 | 87.9 | 8.3 | 100 | 2.0 | 88.8 |
| 0.5 | 3.3 | 2.3 | 89.0 | 5.4 | 100 | 2.2 | 95.1 |
| 0.5 | 2.1 | 1.3 | 90.2 | 6.4 | 100 | 1.9 | 95.1 |
| 0.5 | 3.7 | 2.5 | 88.4 | 5.4 | 100 | 2.3 | 95.2 |
| 0.5 | 2.9 | 1.5 | 88.5 | 7.1 | 100 | 1.9 | 95.1 |
| Average: | 2.8 | 1.8 | 88.8 | 6.5 | 100 | 2.1 | 93.9 |
| 1.0 | 1.3 | 1.1 | 87.4 | 10.2 | 100 | 1.7 | 94.5 |
| 1.0 | 8.7 | 1.4 | 82.9 | 7.0 | 100 | 1.9 | 95.3 |

TABLE I-continued

| Wt-% DCP in Feed | Alkylation Product Composition (Wt-%)[1] | | | | Olefin Conversion (%) | Reid Vapor Pressure[3] | Octane Number[4] |
|---|---|---|---|---|---|---|---|
| | $C_2$–$C_4$ Alkanes | Isopentanes | $C_6$–$C_9$ Alkanes[2] | $C_{10}$+ Hydrocarbons | | | |
| 1.0 | 2.2 | 1.5 | 88.5 | 7.8 | 100 | 1.9 | 95.6 |
| 1.0 | 2.2 | 1.2 | 87.1 | 9.5 | 100 | 1.8 | 94.8 |
| Average: | 3.6 | 1.3 | 86.5 | 8.6 | 100 | 1.8 | 95.1 |

[1]based on product excluding unconverted isobutane.
[2]calculated (as difference)
[3]calculated; given in psi units at 100° F.
[4]calculated; (Research Octane No. + Motor Octane No.)/2

Test data in Table I clearly show that alkylation products which contained the lowest amounts of volatile isopentane and had the lowest vapor pressures were those which were formed when about 0.1–1 weight-% dicyclopentadiene (DCP) was present in the isobutane/butene-2 feed. The presence of about 0.5–1 weight-% dicyclopentadiene in the feed resulted in the most desirable alkylates (which contained the highest percentage of $C_6$–$C_9$ alkanes, had the lowest Reid vapor pressures and had the highest octane numbers).

EXAMPLE II

This example illustrates the effects of the presence of tetrahydrodicyclopentadiene (THDP) in the alkylation process of this invention. The test procedure was essentially the same as the one described in Example I, except that 0–1.0 weight-% tetrahydrodicyclopentadiene (in lieu of dicyclopentadiene) was present in the isobutane/butene-2 feed. Pertinent test results are summarized in Table II.

Test data in Table II clearly show that alkylation products which contained the lowest amounts of volatile isopentane and had the lowest vapor pressures were those which were formed when the isopentane/butene-2 feed also contained about 0.1–1.0 weight-% tetrahydrodicyclopentadiene (THDP).

Reasonable variations, modifications and adaptations for various conditions, which will be apparent to those skilled in the art, can be made within the scope of the disclosure and the appended claims without departing from the scope of this invention.

That which is claimed:

1. In a process for alkylating at least one alkane containing 2–12 carbon atoms per molecule with at least one alkene containing 2–12 carbon atoms per molecule in the presence of a catalyst comprising trifluoromethanesulfonic acid and at least one solid inorganic material so as to produce at least one product alkane containing more carbon atoms than said at least one feed alkane, the improvement which comprises the presence of at least one tricyclic hydrocarbon selected

TABLE II

| Wt-% THDP in Feed | Alkylation Product Composition (Wt-%)[1] | | | | Olefin Conversion (%) | Reid Vapor Pressure[3] | Octane Number[4] |
|---|---|---|---|---|---|---|---|
| | $C_1$–$C_4$ Alkanes | Isopentanes | $C_6$–$C_8$ Alkanes[2] | $C_9$+ Hydrocarbons | | | |
| 0 | 4.3 | 6.6 | 84.8 | 4.3 | 100 | 3.8 | 89.7 |
| 0 | 5.1 | 8.1 | 82.6 | 4.2 | 100 | 4.4 | 92.6 |
| 0 | 5.3 | 8.1 | 76.1 | 10.5 | 100 | 4.3 | 92.4 |
| 0 | 3.3 | 6.9 | 83.5 | 6.3 | 100 | 3.9 | 93.1 |
| Average: | 4.5 | 7.4 | 81.8 | 6.3 | 100 | 4.1 | 92.0 |
| 0.09 | 3.8 | 4.9 | 85.8 | 5.5 | 100 | 3.4 | 89.8 |
| 0.09 | 2.2 | 4.2 | 85.1 | 8.5 | 100 | 3.2 | 88.4 |
| 0.09 | 2.2 | 4.8 | 85.1 | 7.9 | 100 | 3.4 | 88.5 |
| 0.09 | 2.6 | 5.3 | 84.8 | 7.3 | 100 | 3.5 | 88.6 |
| 0.09 | 3.3 | 5.4 | 83.9 | 7.4 | 100 | 3.6 | 88.8 |
| Average: | 2.8 | 4.9 | 84.9 | 7.3 | 100 | 3.4 | 88.8 |
| 0.5 | 2.8 | 3.7 | 83.8 | 9.7 | 100 | 3.0 | 90.9 |
| 0.5 | 3.2 | 3.4 | 83.6 | 9.8 | 100 | 2.9 | 91.0 |
| 0.5 | 2.7 | 2.6 | 84.7 | 10.0 | 100 | 2.6 | 91.1 |
| 0.5 | 9.1 | 5.9 | 78.3 | 6.7 | 100 | 3.8 | 91.4 |
| Average: | 4.4 | 3.9 | 82.6 | 9.1 | 100 | 3.1 | 91.1 |
| 1.0 | 2.7 | 1.7 | 82.2 | 13.4 | 100 | 2.0 | 88.2 |
| 1.0 | 8.7 | 4.5 | 78.2 | 8.6 | 100 | 3.1 | 89.2 |
| 1.0 | 1.3 | 2.0 | 85.2 | 11.5 | 100 | 2.2 | 90.1 |
| 1.0 | 1.9 | 2.7 | 84.3 | 11.1 | 100 | 2.5 | 90.2 |
| Average: | 3.7 | 2.7 | 82.5 | 11.2 | 100 | 2.5 | 89.4 |

[1]based on product excluding unconverted isobutane.
[2]calculated (as difference)
[3]calculated; given in psi units at 100° F.
[4]calculated; (Research Octane No. + Motor Octane No.)/2 from the group consisting of dicyclopentadiene, tetrahydrodicyclopentadiene and mixtures thereof in the feed comprising said at least one feed alkane and said at least one feed alkene.

2. In a process for alkylating at least one alkane containing 2–12 carbon atoms per molecule with at least one alkene containing 2–12 carbon atoms per molecule in the presence of a catalyst comprising trifluoromethanesulfonic acid and at least one solid inorganic material so as to produce at least one product alkane containing more carbon atoms than said at least one feed alkane, the improvement which comprises the presence of dicyclopentadiene in the feed comprising said at least one feed alkane and said at least one feed alkene.

3. A process in accordance with claim 2, wherein the content of dicyclopentadiene in said feed is about 0.05–3.0 weight percent.

4. A process in accordance with claim 3, wherein said at least one solid inorganic material is selected from the group consisting of alumina, silica, silica-alumina, titania, zirconia, aluminum phosphate, aluminum oxide/phosphate, aluminum borate, aluminum borate/oxide, boron oxide, boron phosphate, aluminum boron phosphate, boron sulfate, zirconium sulfate, and mixtures thereof.

5. A process in accordance with claim 4, wherein said at least one solid inorganic material is silica.

6. A process in accordance with claim 3, wherein said at least one feed alkane contains 4–8 carbon atoms per molecule, said at least one feed alkene contains 4–6 carbon atoms per molecule, the content of dicyclopentadiene in said feed is about 0.05–3.0 weight-%, and said at least one solid inorganic is selected from the group consisting of alumina, silica, silica-alumina, titania, zirconia, aluminum phosphate, aluminum oxide/phosphate, aluminum borate, aluminum borate/oxide, boron oxide, boron phosphate, aluminum boron phosphate, boron sulfate, zirconium sulfate, and mixtures thereof.

7. A process in accordance with claim 6, wherein the content of dicyclopentadiene in said feed is about 0.1–1.0 weight-%.

8. A process in accordance with claim 7, wherein the weight ratio of trifluoromethanesulfonic acid to said at least one solid inorganic material is in the range of about 0.01:1 to about 0.4:1.

9. A process in accordance with claim 8, wherein said at least one solid inorganic material is silica.

10. A process in accordance with claim 9, wherein said at least one feed alkane is isobutane and said at least one feed alkene is butene-2.

11. In a process for alkylating at least one alkane containing 2–12 carbon atoms per molecule with at least one alkene containing 2–12 carbon atoms per molecule in the presence of a catalyst comprising trifluoromethanesulfonic acid and at least one solid inorganic material so as to produce at least one product alkane containing more carbon atoms than said at least one feed alkane, the improvement which comprises the presence of tetrahydrocyclopentadiene in the feed comprising said at least one feed alkane and said at least one feed alkene.

12. A process in accordance with claim 11, wherein the content of tetrahydrodicyclopentadiene in said feed is about 0.05–3.0 weight-%.

13. A process in accordance with claim 12, wherein said at least one solid inorganic material is selected from the group consisting of alumina, silica, silica-alumina, titania, zirconia, aluminum phosphate, aluminum oxide/phosphate, aluminum borate, aluminum borate/oxide, boron oxide, boron phosphate, aluminum boron phosphate, boron sulfate, zirconium sulfate, and mixtures thereof.

14. A process in accordance with claim 13, wherein said at least one solid inorganic material is silica.

15. A process in accordance with claim 12, wherein said at least one feed alkane contains 4–8 carbon atoms per molecule, said at least one feed alkene contains 4–6 carbon atoms per molecule, the content of dicyclopentadiene in said feed is about 0.05–3.0 weight-%, and said at least one solid inorganic is selected from the group consisting of alumina, silica, silica-alumina, titania, zirconia, aluminum phosphate, aluminum oxide/phosphate, aluminum borate, aluminum borate/oxide, boron oxide, boron phosphate, aluminum boron phosphate, boron sulfate, zirconium sulfate, and mixtures thereof.

16. A process in accordance with claim 15, wherein the content of tetrahydrodicyclopentadiene in said feed is about 0.1–1.0 weight-%.

17. A process in accordance with claim 16, wherein the weight ratio of trifluoromethanesulfonic acid to said at least one solid inorganic material is in the range of about 0.01:1 to about 0.4:1.

18. A process in accordance with claim 17, where said solid inorganic material is silica.

19. A process in accordance with claim 18, wherein said at least one feed alkane is isobutane and said at least one feed alkene is butene-2.

\* \* \* \* \*